United States Patent [19]

Baker et al.

[11] Patent Number: 5,780,475
[45] Date of Patent: Jul. 14, 1998

[54] ANTIPSYCHOTIC INDAZOLE DERIVATIVES

[75] Inventors: Raymond Baker, Green Tye; Janusz Jozef Kulagowski, Bishops Stortford; Paul David Leeson, Cambridge; Adrian Leonard Smith, Bishops Stortford, all of Great Britain

[73] Assignee: Merck, Sharp & Dohme Limited, Hoddesdon, England

[21] Appl. No.: 525,629

[22] PCT Filed: Mar. 14, 1994

[86] PCT No.: PCT/GB94/00504

§ 371 Date: Dec. 29, 1995

§ 102(e) Date: Dec. 29, 1995

[87] PCT Pub. No.: WO94/21630

PCT Pub. Date: Sep. 29, 1994

[30] Foreign Application Priority Data

Mar. 18, 1993 [GB] United Kingdom .................. 9305623

[51] Int. Cl.$^6$ .................. A61K 31/495; A61K 31/44; A61K 31/415
[52] U.S. Cl. .................. 514/255; 544/357; 544/364; 544/371
[58] Field of Search .................. 544/371, 295, 544/357, 364; 514/255

[56] References Cited

U.S. PATENT DOCUMENTS

| | | | |
|---|---|---|---|
| 3,362,956 | 1/1968 | Archer | 260/268 |
| 3,678,059 | 7/1972 | Gschwend et al. | 260/295.5 B |
| 5,432,177 | 7/1995 | Baker et al. | 514/253 |
| 5,665,732 | 9/1997 | Baker et al. | 514/307 |

FOREIGN PATENT DOCUMENTS

| | | |
|---|---|---|
| 0 281 309 | 9/1988 | European Pat. Off. . |
| 376 607 | 7/1990 | European Pat. Off. . |
| 378 255 | 7/1990 | European Pat. Off. . |
| 0 417 653 | 3/1991 | European Pat. Off. . |
| WO92/17475 | 10/1992 | WIPO . |

OTHER PUBLICATIONS

Dudykina et all "Some derivatives of 3–aminomethyhlindazole", Chem. Abst. vol. 57, No. 10, Nov. 12, 1962 Abst. No. 12467h.

*Primary Examiner*—Phyllis G. Spivack
*Attorney, Agent, or Firm*—Melvin Winokur

[57] ABSTRACT

Disclosed is a class of 1H-indazole derivatives, substituted at the 3-position by a substituted piperazinylmethyl moiety, which are antagonists of dopamine receptor subtypes within the brain, having a selective affinity for the dopamine D4 receptor subtype over other dopamine receptor subtypes, and are accordingly, of benefit in the treatment and/or prevention of psychotic disorders, such as schizophrenia, while manifesting fewer side-effects than those associated with classical neuroleptic drugs.

7 Claims, No Drawings

ANTIPSYCHOTIC INDAZOLE DERIVATIVES

This invention relates to the use of a particular class of heteroaromatic compounds. More particularly, the invention is concerned with the use of substituted indazole derivatives which are antagonists of dopamine receptor subtypes within the brain and are therefore of benefit in the treatment and/or prevention of psychotic disorders such as schizophrenia.

The "dopamine hypothesis" of schizophrenia predicts an increased activity of dopamine neurotransmission in the disease. The hypothesis is supported by early observations that drugs, such as amphetamine, with dopamine agonist or dopamine-releasing properties are capable of eliciting a psychosis indistinguishable from acute paranoid schizophrenia.

Schizophrenia is a disorder which is conventionally treated with drugs known as neuroleptics. In the majority of cases, the symptoms of schizophrenia can be treated successfully with so-called "classical" neuroleptic agents such as haloperidol. Classical neuroleptics generally are antagonists at dopamine $D_2$ receptors. The fact that classical neuroleptic drugs have an action on dopamine receptors in the brain thus lends credence to the "dopamine hypothesis" of schizophrenia.

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., Nature (London), 1991, 350, 610) and $D_5$ (Sunahara et al., Nature (London), 1991, 350, 614) receptor subtypes have been described.

Notwithstanding their beneficial antipsychotic effects, classical neuroleptic agents such as haloperidol are frequently responsible for eliciting acute extrapyramidal symptoms and neuroendocrine disturbances. These side-effects, which clearly detract from the clinical desirability of classical neuroleptics, are believed to be attributable to $D_2$ receptor blockade in the striatal region of the brain. It is considered (Van Tol et al., supra) that compounds which can interact selectively with the dopamine $D_4$ receptor subtype, whilst having a less-pronounced action at the $D_2$ subtype, might be free from, or at any rate less prone to, the side-effects associated with classical neuroleptics, whilst at the same time maintaining a beneficial level of antipsychotic activity.

The compounds of use in the present invention, being antagonists of dopamine receptor subtypes within the brain, are accordingly of benefit in the treatment and/or prevention of psychotic disorders such as schizophrenia. Moreover, the compounds of use in the invention have a selective affinity for the dopamine $D_4$ receptor subtype over other dopamine receptor subtypes, in particular the $D_2$ subtype, and can therefore be expected to manifest fewer side-effects than those associated with classical neuroleptic drugs.

U.S. Pat. No. 3,362,956 describes certain 1-|(heterocyclyl)-lower-alkyl|-4-substituted-piperazines, in which the heterocyclyl moiety represents inter alia an indazole group (also referred to therein as a 2-azaindole group). These compounds are alleged therein to possess a panoply of depressant actions on the autonomic nervous system, the cardiovascular system and the skeletal muscular system (including psychomotor depressant, sedative, adrenolytic, rectal temperature lowering, anticonvulsant, blood pressure lowering and heart force increasing activities), and are consequently alleged to be useful as tranquilizers, sedatives, adrenolytic agents, hypothermic agents, anti-convulsants, hypotensive agents and cardiovascular agents.

A related series of compounds, which are stated to be cholinesterase inhibitors and thus useful in enhancing memory in patients suffering from dementia and Alzheimer's disease, is described in WO-A-92/17475.

The disclosure of U.S. Pat. No. 3,678,059 generically encompasses inter alia a class of 3-|piperazin-1-ylalkyl| indazole derivatives substituted on the indazole nitrogen atom by an araliphatic or aromatic radical. These compounds are alleged therein to possess antidepressant and anti-inflammatory activity.

There is, however, no suggestion in U.S. Pat. Nos. 3,362,956 or 3,678,059, or in WO-A-92/17475, that the compounds described therein would be of any benefit in the treatment and/or prevention of psychotic disorders such as schizophrenia, still less that in doing so they might be expected to manifest fewer side-effects than those exhibited by classical neuroleptic agents.

The present invention accordingly provides the use of a compound of formula I, or a pharmaceutically acceptable salt thereof or a prodrug thereof:

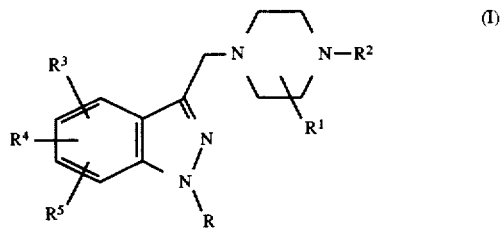

wherein

R represents hydrogen or $C_{1-6}$ alkyl;

$R^1$ represents hydrogen, or an optionally substituted $C_{1-6}$ alkyl, $C_{1-6}$ alkoxy, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, aryl($C_{1-6}$)alkoxy, aryl($C_{2-6}$)alkenyl, aryl($C_{2-6}$)alkynyl, heteroaryl, heteroaryl($C_{1-6}$)alkyl, heteroaryl($C_{2-6}$)alkenyl or heteroaryl($C_{2-6}$)alkynyl group;

$R^2$ represents an optionally substituted $C_{1-6}$ alkyl, $C_{1-6}$ alkoxy, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, aryl($C_{1-6}$) alkoxy, aryl($C_{2-6}$)alkenyl, aryl($C_{2-6}$)alkynyl, heteroaryl, heteroaryl($C_{1-6}$)alkyl, heteroaryl($C_{2-6}$) alkenyl or heteroaryl($C_{2-6}$)alkynyl group;

$R^3$, $R^4$ and $R^5$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$; and $R^a$ and $R^b$ independently represent hydrogen, hydrocarbon or a heterocyclic group; for the manufacture of a medicament for the treatment and/or prevention of psychotic disorders such as schizophrenia.

For use in medicine, the salts of the compounds of formula I will be pharmaceutically acceptable salts. Other salts may, however, be useful in the preparation of the compounds of use in the invention or of their pharmaceutically acceptable salts. Suitable pharmaceutically acceptable salts of the compounds of use in this invention include acid addition salts which may, for example, be formed by mixing a solution of the compound of use in the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of use in the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbons" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl and aryl($C_{2-6}$)alkynyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl, heteroaryl($C_{1-6}$)alkyl, heteroaryl($C_{2-6}$)alkenyl and heteroaryl($C_{2-6}$)alkynyl groups.

Suitable alkyl groups within the scope of the term "hydrocarbon" and within the definition of the substituents R, $R^1$ and $R^2$ include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl and t-butyl.

Suitable alkenyl groups within the scope of the term "hydrocarbon" and within the definition of the substituents $R^1$ and $R^2$ include straight-chained and branched alkenyl groups containing from 2 to 6 carbon atoms. Typical examples include vinyl and allyl groups.

Suitable alkynyl groups within the scope of the term "hydrocarbon" and within the definition of the substituents $R^1$ and $R^2$ include straight-chained and branched alkynyl groups containing from 2 to 6 carbon atoms. Typical examples include ethynyl and propargyl groups.

Suitable cycloalkyl groups within the scope of the term "hydrocarbon" and within the definition of the substituents $R^1$ and $R^2$ include groups containing from 3 to 7 carbon atoms. Particular cycloalkyl groups are cyclopropyl and cyclohexyl.

Particular cycloalkyl($C_{1-6}$)alkyl groups within the scope of the term "hydrocarbon" and within the definition of the substituents $R^1$ and $R^2$ include cyclopropylmethyl, cyclohexylmethyl and cyclohexylethyl.

Particular aryl groups within the scope of the term "hydrocarbon" and within the definition of the substituents $R^1$ and $R^2$ include phenyl and naphthyl.

Particular aryl($C_{1-6}$)alkyl groups within the scope of the term "hydrocarbon" and within the definition of the substituents $R^1$ and $R^2$ include benzyl, naphthylmethyl, phenethyl and phenylpropyl.

Suitable heterocycloalkyl groups include azetidinyl, pyrrolidyl, piperidyl, piperazinyl and morpholinyl groups.

Suitable heteroaryl groups within the scope of the expression "a heterocyclic group" and within the definition of the substituents $R^1$ and $R^2$ include pyridyl, quinolyl, isoquinolyl, pyridazinyl, pyrimidinyl, pyrazinyl, pyranyl, furyl, benzofuryl, dibenzofuryl, thienyl, benzthienyl, imidazolyl, oxadiazolyl and thiadiazolyl groups.

Particular heteroaryl($C_{1-6}$)alkyl groups within the scope of the expression "a heterocyclic group" and within the definition of the substituents $R^1$ and $R^2$ include thienylmethyl, pyridylmethyl, pyrimidinylmethyl and pyrazinylmethyl.

The hydrocarbon and heterocyclic groups, as well as the substituents $R^1$ and $R^2$, may in turn be optionally substituted by one or more groups selected from $C_{1-6}$ alkyl, adamantyl, phenyl, aryl($C_{1-6}$)alkyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —NR'R'', —NR''COR'', —NR''CO$_2$R'', —NR''SO$_2$R'', —CH$_2$NR''SO$_2$R'', —NHCONR''R'', —CONR''R'', —SO$_2$NR'R'' and —CH$_2$SO$_2$NR'R'', in which R' and R'' independently represent hydrogen, $C_{1-6}$ alkyl, aryl or aryl($C_{1-6}$)alkyl.

The term "halogen" as used herein includes fluorine, chlorine, bromine and iodine, especially chlorine.

The present invention includes within its scope the use of prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Where the compounds of use in the invention have at least one asymmetric centre, they may accordingly exist as enantiomers. Where the compounds of use in the invention possess two or more asymmetric centres, they may additionally exist as diastereoisomers. It is to be understood that the use of all such isomers and mixtures thereof is encompassed within the scope of the present invention.

Suitably, the substituent R represents hydrogen or methyl, especially hydrogen.

Suitably, the substituent $R^1$ represents hydrogen or methyl, especially hydrogen.

Suitable values for the substituent $R^2$ include $C_{1-6}$ alkyl, $C_{3-7}$ cycloalkyl($C_{1-6}$)alkyl, aryl, aryl($C_{1-6}$)alkyl and heteroaryl, any of which groups may be optionally substituted. Examples of optional substituents on the group $R^2$ include $C_{1-6}$ alkyl, halogen, trifluoromethyl, $C_{1-6}$ alkoxy, keto, $C_{1-3}$ alkylenedioxy, nitro and $C_{2-6}$ alkylcarbonyl.

Particular values of $R^2$ include methyl, ethyl, n-propyl, isopropyl, cyclohexyl-ethyl, phenyl, methylphenyl, ethylphenyl, fluorophenyl, chlorophenyl, trifluoromethylphenyl, bis(trifluoromethyl)-phenyl, methoxyphenyl, methylenedioxy-phenyl, acetylphenyl, nitrophenyl, benzyl, chlorobenzyl, methylenedioxy-benzyl, benzylcarbonyl, phenethyl, pyridyl, chloropyridyl, methylpyridyl, trifluoromethyl-pyridyl, methoxypyridyl, quinolyl, isoquinolyl and pyrimidinyl.

Suitable values for the substituents $R^3$, $R^4$ and $R^5$ include hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy and $C_{2-6}$ alkylcarbonyl. Particular values include hydrogen, fluoro, chloro, iodo, methyl, methoxy and benzyloxy.

A particular sub-class of compounds of use in the invention is represented by the compounds of formula IIA, and pharmaceutically acceptable salts thereof and prodrugs thereof:

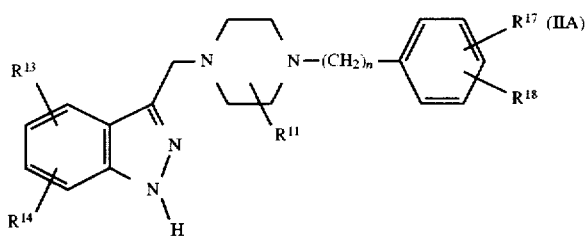

(IIA)

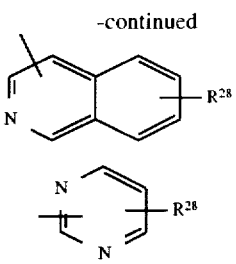

(Yc)

(Yd)

wherein n is zero, 1, 2 or 3;

$R^{11}$ represents hydrogen or $C_{1-6}$ alkyl;

$R^{13}$ and $R^{14}$ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$) alkoxy or $C_{2-6}$ alkylcarbonyl; or $R^{13}$ and $R^{14}$, when situated on adjacent carbon atoms, together represent methylenedioxy; and $R^{17}$ and $R^{18}$ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$) alkoxy or $C_{2-6}$ alkylcarbonyl; or $R^{17}$ and $R^{18}$, when situated on adjacent carbon atoms, together represent methylenedioxy.

Particular values of $R^{11}$ include hydrogen and methyl, especially hydrogen.

Particular values of $R^{13}$ and $R^{14}$ include hydrogen, halogen, methyl, ethyl, methoxy and benzyloxy, especially hydrogen, fluoro, chloro and iodo. Suitably, one of $R^{13}$ and/or $R^{14}$ is hydrogen.

Particular values of $R^{17}$ and $R^{18}$ include hydrogen, fluoro, chloro, trifluoromethyl, methyl, methoxy, acetyl and nitro. Suitably, one of $R^{17}$ and/or $R^{18}$ is hydrogen.

In a subset of the compounds of formula IIA above, $R^{14}$ and $R^{18}$ both represent hydrogen.

Another sub-class of compounds of use in the invention is represented by the compounds of formula IIB, and pharmaceutically acceptable salts thereof and prodrugs thereof:

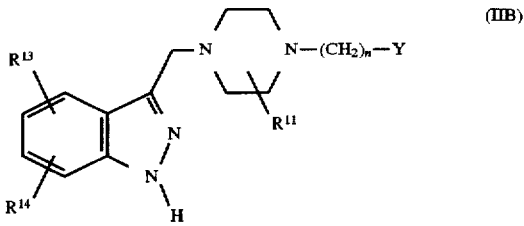

(IIB)

wherein n, $R^{11}$, $R^{13}$ and $R^{14}$ are as defined with reference to formula IIA above; and Y represents a group of formula Ya, Yb, Yc or Yd:

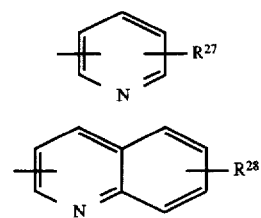

(Ya)

(Yb)

in which $R^{27}$ represents halogen, trifluoromethyl, $C_{1-6}$ alkyl or $C_{1-6}$ alkoxy; and $R^{28}$ represents hydrogen, halogen, trifluoromethyl, $C_{1-6}$ alkyl or $C_{1-6}$ alkoxy.

Particular values of $R^{27}$ include chloro, trifluoromethyl, methyl and methoxy.

Particular values of $R^{28}$ include hydrogen, chloro, trifluoromethyl, methyl and methoxy, especially hydrogen.

In a subset of the compounds of formula IIB above, $R^{14}$ represents hydrogen, Y represents a group of formula Ya, Yb or Yc, and $R^{27}$ and $R^{28}$ are other than trifluoromethyl.

Certain compounds falling within the scope of formula I above are novel. A particular sub-class of novel compounds in accordance with the present invention comprises the compounds of formula IIB as defined above, and salts and prodrugs thereof. The invention further provides a novel compound selected from the following:

3-|4-(4-chlorophenyl)piperazin-1-ylmethyl|-1H-indazole;
3-(4-phenylpiperazin-1-ylmethyl)-1H-indazole;
3-(4-benzylpiperazin-1-ylmethyl)-1H-indazole;
3-(3-methyl-4-phenylpiperazin-1-ylmethyl)-1H-indazole;
3-|4-(4-fluorophenyl)piperazin-1-ylmethyl|-1H-indazole;
3-|4-(2-methylphenyl)piperazin-1-ylmethyl|-1H-indazole;
3-|4-(3-methylphenyl)piperazin-1-ylmethyl|-1H-indazole;
3-|4-(4-methylphenyl)piperazin-1-ylmethyl|-1H-indazole;
3-|4-(pyrimidin-2-yl)piperazin-1-ylmethyl|-1H-indazole;
3-|4-(3,4-methylenedioxybenzyl)piperazin-1-ylmethyl|-1H-indazole;
3-|4-(3-trifluoromethylphenyl)piperazin-1-ylmethyl|-1H-indazole;
3-|4-(pyrid-2-yl)piperazin-1-ylmethyl|-1H-indazole;
3-|4-(4-methoxyphenyl)piperazin-1-ylmethyl|-1H-indazole;
3-|4-(4-acetylphenyl)piperazin-1-ylmethyl|-1H-indazole;
6-fluoro-3-|4-(4-methoxyphenyl)piperazin-1-ylmethyl|-1H-indazole;
3-|4-(4-chlorophenyl)piperazin-1-ylmethyl|-6-fluoro-1H-indazole;
6-fluoro-3-|4-(2-phenylethyl)piperazin-1-ylmethyl|-1H-indazole;
6-chloro-3-|4-(4-methoxyphenyl)piperazin-1-ylmethyl|-1H-indazole;
7-chloro-3-|4-(4-methoxyphenyl)piperazin-1-ylmethyl|-1H-indazole;
3-|4-(2-phenylethyl)piperazin-1-ylmethyl|-1H-indazole;
3-|4-(5-chloropyrid-2-yl)piperazin-1-ylmethyl|-1H-indazole;
3-|4-(5-methylpyrid-2-yl)piperazin-1-ylmethyl|-1H-indazole;
3-|4-(5-methoxypyrid-2-yl)piperazin-1-ylmethyl|-1H-indazole;
3-|4-(quinolin-2-yl)piperazin-1-ylmethyl|-1H-indazole;
3-|4-(isoquinolin-3-yl)piperazin-1-ylmethyl|-1H-indazole;
3-|4-(3,4-methylenedioxyphenyl)piperazin-1-ylmethyl|-1H-indazole;
3-|4-(3,5-bis(trifluoromethyl)phenyl)piperazin-1-ylmethyl|-1H-indazole;

3-[4-(5-trifluoromethylpyrid-2-yl)piperazin-1-ylmethyl]-1H-indazole;

3-[4-(4-trifluoromethylpyrid-2-yl)piperazin-1-ylmethyl]-1H-indazole;

3-(4-benzylcarbonylpiperazin-1-ylmethyl)-6-fluoro-1H-indazole;

7-iodo-3-[4-(4-methoxyphenyl)piperazin-1-ylmethyl]-1H-indazole;

7-fluoro-3-[4-(4-methoxyphenyl)piperazin-1-ylmethyl]-1H-indazole;

7-fluoro-3-[4-(4-methylphenyl)piperazin-1-ylmethyl]-1H-indazole;

6,7-difluoro-3-[4-(4-methoxyphenyl)piperazin-1-ylmethyl]-1H-indazole;

3-[4-(4-chlorophenyl)piperazin-1-ylmethyl]-6,7-difluoro-1H-indazole;

7-chloro-3-[4-(4-chlorophenyl)piperazin-1-ylmethyl]-1H-indazole;

7-chloro-3-[4-(3,4-methylenedioxyphenyl)piperazin-1-ylmethyl]-1H-indazole;

7-chloro-3-[4-(3-trifluoromethylphenyl)piperazin-1-ylmethyl]-1H-indazole;

7-chloro-3-[4-(4-methylphenyl)piperazin-1-ylmethyl]-1H-indazole;

7-chloro-3-[4-(5-chloropyrid-2-yl)piperazin-1-ylmethyl]-1H-indazole;

7-chloro-3-[4-(isoquiolin-3-yl)piperazin-1-ylmethyl]-1H-indazole;

and salts and prodrugs thereof.

The invention also provides pharmaceutical compositions comprising one or more of the novel compounds according to the invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds of formula I above, including the novel compounds according to the present invention, may be prepared by a process which comprises reacting a compound of formula III with a compound of formula IV:

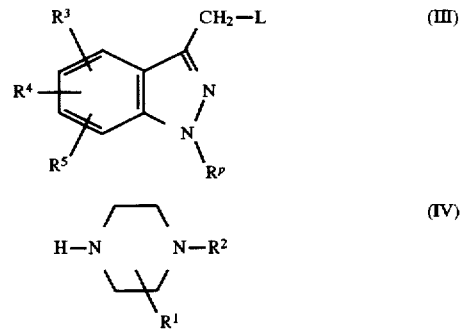

wherein $R^1$, $R^2$, $R^3$, $R^4$ and $R^5$ are as defined above, L represents a suitable leaving group, and $R^p$ corresponds to the group R as defined above or represents a suitable protecting group; followed, where required, by removal of the protecting group $R^p$; and subsequently, if necessary, N-alkylation by standard methods to introduce the moiety R.

The leaving group L is suitably a halogen atom, e.g. bromine.

The protecting group $R^p$ on the indazole nitrogen atom, when present, is suitably an acyl moiety such as acetyl, which can conveniently be removed as necessary by treatment under strongly basic conditions, e.g. sodium methoxide in methanol. Alternatively, the protecting group $R^p$ may be a carbamoyl moiety such as t-butoxycarbonyl (BOC), which can conveniently be removed as necessary by treatment under mildly acidic conditions.

The reaction between compounds III and IV is conveniently carried out by stirring the reactants under basic conditions in a suitable solvent, for example potassium carbonate in N,N-dimethylformamide; triethylamine in tetrahydrofuran or acetonitrile; or diisopropylethylamine (Hünig's base) in dichloromethane.

In an alternative procedure, the compounds of formula I above, including the novel compounds according to the present invention, may be prepared by a process which comprises reducing a compound of formula V:

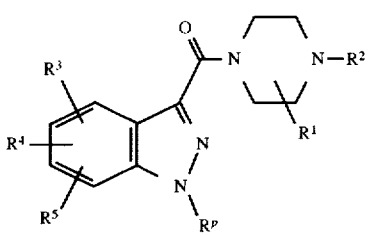

wherein $R^1$, $R^2$, $R^3$, $R^4$, $R^5$ and $R^p$ are as defined above; followed, where required, by removal of the protecting group $R^p$; and subsequently, if necessary, N-alkylation by standard methods to introduce the moiety R.

The reaction is conveniently carried out by treating the compound V with a reducing agent such as lithium aluminium hydride in an appropriate solvent, e.g. tetrahydrofuran.

The intermediates of formula V above may suitably be prepared by reacting a compound of formula IV as defined above with a compound of formula VI:

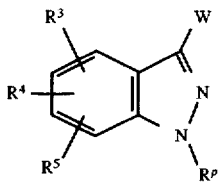

wherein $R^3$, $R^4$, $R^5$ and $R^p$ are as defined above; and W represents a reactive carboxylate moiety.

Suitable values for the reactive carboxylate moiety W include esters, for example $C_{1-4}$ alkyl esters; acid anhydrides, for example mixed anhydrides with $C_{1-4}$ alkanoic acids; acid halides, for example acid chlorides; and acylimidazoles.

By way of example, the intermediates of formula VI above wherein W is an acid chloride moiety may be prepared by treating the corresponding carboxylic acid derivative with thionyl chloride in toluene. Similarly, the intermediates of formula VI wherein W is an acylimidazole moiety may be prepared by treating the corresponding carboxylic acid derivative with 1,1'-carbonyldiimidazole. Alternatively, the reactive carboxylate moiety W may be obtained by treating the corresponding compound wherein W is carboxy with 1-(3-dimethylaminopropyl)-3-ethylcarbodiimide hydrochloride and 1-hydroxybenzotriazole hydrate, optionally in the presence of triethylamine; the resulting activated carboxylate intermediate may then suitably be reacted in situ with the required compound of formula IV.

Where they are not commercially available, the starting materials of formula III, IV and VI may be prepared by procedures analogous to those described in the accompanying Examples, or by standard methods well known from the art.

It will be appreciated that any compound of formula I initially obtained from any of the above processes may, where appropriate, subsequently be elaborated into a further desired compound of formula I using techniques known from the art. For example, a compound of formula I wherein R is hydrogen initially obtained may be converted into a compound of formula I wherein R represents $C_{1-6}$ alkyl by standard alkylation techniques, such as by treatment with an alkyl iodide, e.g. methyl iodide, typically under basic conditions, e.g. sodium hydride in dimethylformamide, or triethylamine in acetonitrile.

Where the above-described processes for the preparation of the compounds of use in the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

The following Examples illustrate the preparation of compounds according to the invention.

The compounds useful in this invention potently inhibit $[^3H]$-spiperone binding to human dopamine $D_4$ receptor subtypes expressed in clonal cell lines.

$[^3H]$-Spiperone Binding Studies

Clonal cell lines expressing the human dopamine $D_4$ receptor subtype were harvested in PBS and then lysed in 10 mM Tris-HCl pH 7.4 buffer containing 5 mM $MgSO_4$ for 20 min on ice. Membranes were centrifuged at 50,000 g for 15 min at 4° C. and the resulting pellets resuspended in assay buffer (50 mM Tris-HCl pH 7.4 containing 5 mM EDTA, 1.5 mM $CaCl_2$, 5 mM $MgCl_2$, 5 mM KCl, 120 mM NaCl, and 0.1% ascorbic acid) at 20 mg/ml wet weight. Incubations were carried out for 60 min at room temperature (22° C.) in the presence of 0.05–2 nM $[^3H]$-spiperone or 0.2 nM for displacement studies and were initiated by addition of 20–100 μg protein in a final assay volume of 0.5 ml. The incubation was terminated by rapid filtration over GF/B filters presoaked in 0.3% PEI and washed with 10 ml ice-cold 50 mM Tris-HCl, pH 7.4. Specific binding was determined by 10 μM apomorphine and radioactivity determined by counting in a LKB beta counter. Binding parameters were determined by non-linear least squares regression analysis, from which the inhibition constant $K_i$ could be calculated for each test compound.

The compounds of the accompanying Examples were tested in the above assay, and all were found to possess a $K_i$ value for displacement of $[^3H]$-spiperone from the human dopamine $D_4$ receptor subtype of below 1.5 μM.

EXAMPLES

General techniques: All reactions were carried out under a nitrogen atmosphere using anhydrous solvents under anhydrous conditions unless otherwise noted. Yields refer to chromatographically (HPLC/TLC) and spectroscopically ($^1H$ NMR) homogeneous materials, unless otherwise stated.

All reactions were monitored by thin-layer chromatography carried out on 0.25 mm E. Merck silica gel plates (60F-254) using UV light and/or $I_2$ vapour for visualisation. Fluka silica gel (60, particle size 0.035–0.070 mm) was used for flash chromatography.

Example 1

3-[4-(4-Chlorophenyl)piperazin-1-ylmethyl]-1H-indazole

1H-Indazole-3-carboxylic acid (0.774 g, 4.78 mmol), 1-(4-chlorophenyl)piperazine dihydrochloride (2.15 g, 8 mmol), 1-hydroxybenzotriazole hydrate (1.11 g, 8 mmol) and 1-(3-dimethylaminopropyl)-3-ethylcarbodiimide hydrochloride (1.57 g, 8 mmol) were suspended in $CH_2Cl_2$ (50 mL) and treated with N-N-diisopropylethylamine (Hünig's base, 2.79 mL, 16 mmol). The mixture was stirred at 20° C. for 14 h during which time the suspension dissolved.

The solution was poured into water (100 mL) and extracted with $CH_2Cl_2$ (3×100 mL). The combined organic extracts were dried ($MgSO_4$) and concentrated. The residue was dissolved in refluxing EtOAc (50 mL), filtered and concentrated to five a yellow solid (2.215 g).

A suspension of the above solid (2.215 g, 6.50 mmol) in THF (20 mL) was treated with $LiAlH_4$ (9.75 mL of a 1.0M solution in THF, 9.75 mmol) and the resulting solution was heated at 40° C. for 14 h. The solution was cooled, quenched by the cautious addition of 2M aqueous NaOH (1.6 mL), stirred for 1 h at 20° C., filtered washing with EtOAc, and the filtrate was concentrated and the residue purified by flash chromatography (50%→75% EtOAc in hexane) to give the title compound as a white solid (910 mg, 58% based upon 1H-indazole-3-carboxylic acid). This was recrystallised from EtOAc to give a fluffy white crystalline solid; mp 223°–224° C. (from EtOAc); $^1$H NMR (360 MHz, $d_6$-DMSO) δ12.82 (bs, 1H, NH), 7.87 (d, J=8.1 Hz, 1H, indazole), 7.48 (d, J=8.4 Hz, 1H, indazole), 7.33 (dd, J=7.1, 8.1 Hz, 1H, indazole), 7.20 (d, J=9.1 Hz, 2H, Ph), 7.09 (dd, J=7.4, 8.4 Hz, 1H, indazole), 6.91 (d, J=9.1 Hz, 2H, Ph), 3.88 (s, 2H, indazole-$CH_2$—N), 3.11 (bt, J=4.8 Hz, 4H, piperazine), 2.57 (bt, J=5.0 Hz, 4H, piperazine); MS (CI+) m/e 327/329 (3:1, M+H$^+$); Anal. calcd for $C_{18}H_{19}N_4Cl$: C, 66.15;H, 5.86; N, 17.14. Found: C, 66.48;H, 5.87; N, 16.92.

Example 2

3-[4-Phenylpiperazin-1-ylmethyl]-1H-indazole

The title compound was prepared as a fluffy white crystalline solid following the general procedure described in EXAMPLE 1; mp 196°–197° C. (from $Et_2O$); $^1$H NMR (360 MHz, $d_6$-DMSO) δ7.88 (d, J=8.1 Hz, 1H, indazole), 7.49 (d, J=8.4 Hz, 1H, indazole), 7.33 (dd, J=7.6, 8.1 Hz, 1H, indazole), 7.18 (t, J=8.7 Hz, 2H, Ph), 7.09 (dd, J=7.6, 8.4 Hz, 1H, indazole), 6.90 (d, J=8.0 Hz, 2H, Ph), 6.75 (t, J=7.2 Hz, 1H, Ph), 3.89 (2 H, s, indazole-$CH_2$—N), 3.11 (bt, J=5.1 Hz, 4H, piperazine), 2.58 (bt, J=5.1 Hz, 4H, piperazine); MS (CI+) m/e 293 (M+H$^+$); Anal. calcd for $C_{18}H_{20}N_4$: C, 73.94;H, 6.90; N, 19.16. Found: C, 73.89;H, 6.88; N, 18.91.

Example 3

3-[4-Benzylpiperazin-1-ylmethyl]-1H-indazole

The title compound was prepared as a white crystalline solid following the general procedure described in EXAMPLE 1; mp 130°–131 ° C. (from $Et_2O$); $^1$H NMR (360 MHz, $d_6$-DMSO) δ7.84 (d, J=8.1 Hz, 1H, indazole), 7.47 (d, J=8.4 Hz, 1H, indazole), 7.33–7.20 (m, 6H, aromatic), 7.07 (t, J=7.4 Hz, 1H, indazole), 3.81 (s, 2H, indazole-$CH_2$—N ), 3.43 (s, 2H, $CH_2$Ph), 2.43 (bs, 4H, piperazine), 2.36 (bs, 4H, piperazine); MS (CI+) m/e 307 (M+H$^+$); Anal. calcd for $C_{19}H_{22}N_4$: C, 74.48;H, 7.24; N, 18.29. Found: C, 74.43;H, 7.22; N, 18.57.

Example 4

(+)-3-[4-Phenyl-3-methylpiperazin-1-ylmethyl]-1H-indazole

The title compound was prepared as a white crystalline solid following the general procedure described in EXAMPLE 1; mp 164.5°–165.0° C. (from $Et_2O$); $^1$H NMR (360 MHz, $d_6$-DMSO) δ12.80 (bs, 1H, NH), 7.91 (d, J=8.2 Hz, 1H, indazole), 7.49 (d, J=8.4 Hz, 1H, indazole), 7.33 (dd, J=6.0, 7.0 Hz, 1H, indazole), 7.18 (t, J=7.4 Hz, 2H, Ph), 7.09 (t, J=7.2 Hz, 1H, indazole), 6.85 (d, J=8.1 Hz, 2H, Ph), 6.71 (t, J=7.3 Hz, 1H, Ph), 3.97–3.95 (m, 1H, CH—Me), 3.85 (s, 2H, indazole-$CH_2$—N), 3.26–3.21 (m, 1H, piperazine), 2.97–2.84 (m, 2H, piperazine), 2.71–2.68 (m, 1H, piperazine), 2.43–2.39 (m, 1H, piperazine), 2.25–2.18 (m, 1H, piperazine), 0.96 (d, J=5.7 Hz, 3H, Me); MS (CI+) m/e 307 (M+H$^+$); Anal. calcd for $C_{19}H_{22}N_4$: C, 74.48; H, 7.24; N, 18.29. Found: C, 74.53;H, 7.28; N, 18.11.

Example 5

3-[4-(4-Fluorophenyl)piperazin-1-ylmethyl]-1H-indazole

Step A: 1-Acetyl-3-methyl-1H-indazole

3-Methyl-1H-indazole (6.157 g, 44.6 mmol) in $CH_2Cl_2$ (100 mL) was treated with acetic anhydride (22.75 g, 223 mmol), triethylamine (22.5 g, 223 mmol) and DMAP (0.54 g, 4.5 mmol).

The mixture was stirred 1 h at 20° C., poured into water (100 mL) and extracted with $CH_2Cl_2$ (2×100 mL). The extracts were dried ($Na_2SO_4$), concentrated and the residue recrystallised from hexane to give the title compound (4.12 g, 66%) as a white crystalline solid; mp 70°–71° C. (from hexane); $^1$H NMR (360 MHz, $CDCl_3$) δ8.41 (d, J=8.4 Hz, 1H, indazole), 7.64 (d, J=8.4 Hz, 1H, indazole), 7.54 (t, J=8.4 Hz, 1H, indazole), 7.35 (t, J=8.4 Hz, 1H, indazole), 2.75 (s, 3H, Ac), 2.58 (s, 3H, Me); MS (CI+) m/e 175 (M+H$^+$); Anal. calcd for $C_{10}H_{10}N_2O$: C, 68.95, H, 5.97; N, 16.08. Found: C, 68.80;H, 5.58; N, 16.18.

Step B: 1-Acetyl-3-bromomethyl-1H-indazole

1-Acetyl-3-methyl-1H-indazole (5.77 g, 33.1 mmol) in $CCl_4$ (150 mL) was treated with N-bromosuccinimide (6.49 g, 36.5 mmol) and benzoyl peroxide (0.80 g, 3.3 mmol) and the mixture was heated at 70 ° C. for 16 h. The mixture was concentrated and the residue quickly filtered through a plug of flash silica eluting with 0→5% EtOAc in hexane to give the crude title compound contaminated with traces of dibromide and starting material. This was conveniently used directly in subsequent reactions without further purification.

Step C: 1-Acetyl-3-[4-(4-fluorophenyl)piperazin-1-ylmethyl]-1H-indazole

1-Acetyl-3-bromomethyl-1H-indazole (160 mg, 0.63 mmol) in $CH_2Cl_2$ (5 mL) was treated with 1-(4-fluorophenyl)piperazine (228 mg, 1.26 mmol) and Hünig's base (102 mg, 0.79 mmol) and the mixture stirred at 20° C. for 16 h. The mixture was poured into saturated aqueous sodium bicarbonate solution (10 mL) and extracted with $CH_2Cl_2$ (3×10 mL). The combined organic extracts were dried ($MgSO_4$), concentrated and the residue purified by flash chromatography (10%→25% EtOAc in hexane) to give the title compound as a white solid. This was recrystallised from ether/hexane to give colourless crystals (184 mg, 83%); mp 119°–120° C. (from ether/hexane); $^1$H NMR (360 MHz, $d_6$-DMSO) δ8.31 (d, J=8.3 Hz, 1 H, indazole), 8.08 (d, J=8.3 Hz, 1H, indazole), 7.63 (t, J=8.3 Hz, 1H, indazole), 7.43 (t, J=8.3 Hz, 1H, indazole), 7.03 (m, 2H, Ph), 6.93 (m, 2H, Ph), 3.95 (s, 2H, Ar—$CH_2$N), 3.08 (m, 4H, piperazine), 2.70 (s, 3H, Ac), 2.64 (m, 4H, piperazine); MS (CI+) m/e 353 M+H$^+$); Anal. calcd for $C_{20}H_{21}N_4OF$: C, 68.16; H, 6.01; N, 15.90. Found: C, 68.15;H, 5.85; N, 15.64.

Step D: 3-[4-(4-Fluorophenyl)piperazin-1-ylmethyl]-1H-indazole

1-Acetyl-3-[4-(4-fluorophenyl)piperazin-1-ylmethyl]-1H-indazole (112 mg, 0.32 mmol) in MeOH (3 mL) was treated with sodium methoxide (50 mg) and stirred for 1 h at 20° C. The mixture was poured into saturated aqueous sodium bicarbonate solution (5 mL) and extracted with $CH_2Cl_2$ (3×5 mL). The combined organic extracts were dried ($MgSO_4$), concentrated and the residue purified by flash chromatography (10→100% EtOAc in hexane) to give the title compound as a white solid (52 mg, 52%); mp 191°–192° C. (from $CH_2Cl_2$/hexane); $^1$H NMR (360 MHz, $d_6$-DMSO) δ12.85 (bs, 1H, NH), 7.88 (d, J=8.9 Hz, 1H, indazole), 7.49 (d, J=8.9 Hz, 1H, indazole), 7.33 (t, J=8.9 Hz, 1H, indazole), 7.09 (t, J=8.9 Hz, 1H, indazole), 7.00 (m, 2 H, Ph), 6.92 (m, 2H, Ph), 3.89 (s, 2H, Ar—$CH_2$N), 3.06 (m, 4H, piperazine), 2.58 (m, 4H, piperazine); MS (CI+) m/e 311 M+H$^+$); Anal. calcd for $C_{18}H_{19}N_4F\cdot\frac{1}{4}H_2O$: C, 68.66; H, 6.24; N, 17.79. Found: C, 68.75; H, 6.13; N, 17.74.

Example 6

3-[4-(2-Methylphenyl)piperazin-1-ylmethyl]-1H-indazole

The title compound was prepared as a white crystalline solid following the general procedure described in EXAMPLE 5; mp 135°–136° C. (from ether/hexane); $^1$H NMR (360 MHz, $d_6$-DMSO) δ12.82 (bs, 1H, NH), 7.89 (d, J=8.2 Hz, 1H, indazole), 7.49 (d, J=8.2 Hz, 1H, indazole), 7.33 (t, J=8.2 Hz, 1H, indazole), 7.12 (t, J=8.2 Hz, 1H, indazole), 7.10 (m, 2H, Ph, 6.99 (d, J=7.5 Hz, 1H, Ph), 6.92 (t, J=7.5 Hz, 1H, Ph), 3.90 (s, 2H, Ar—$CH_2$N), 2.82 (m, 4H, piperazine), 2.60 (bs, 4H, piperazine), 2.21 (s, 3H, Me); MS (CI+) m/e 307 (M+H$^+$); Anal. calcd for $C_{19}H_{22}N_4$: C, 74.48;H, 7.24; N, 18.29. Found: C, 74.18; H, 7.28; N, 18.37.

Example 7

3-[4-(3-Methylphenyl)piperazin-1-ylmethyl]-1H-indazole

The title compound was prepared as a white crystalline solid following the general procedure described in EXAMPLE 5; mp 132°–134° C. (from $CH_2Cl_2$/hexane); $^1$H NMR (360 MHz, $d_6$-DMSO) δ12.83 (bs, 1H, NH), 7.88 (d, J=8.1 Hz, 1H, indazole), 7.48 (d, J=8.1 Hz, 1H, indazole), 7.33 (t, J=8.1 Hz, 1H, indazole), 7.09 (t, J=8.1 Hz, 1H, indazole), 7.06 (t, J=7.8 Hz, 1H, Ph), 6.72 (s, 1H, Ph), 6.69 (d, J=7.8 Hz, 1H, Ph), 6.57 (d, J=7.8 Hz, 1H, Ph), 3.88 (s, 2H, Ar—$CH_2$N), 3.09 (m, 4H, piperazine), 2.56 (m, 4H, piperazine), 2.22 (s, 3H, Me); MS (CI+) m/e 307 (M+H$^+$); Anal. calcd for $C_{19}N_{22}N_4$: C, 74.48;H, 7.24; N, 18.29. Found: C, 74.05;H, 7.24; N, 18.28.

Example 8

3-[4-(4-Methylphenyl)piperazin-1-ylmethyl]-1H-indazole

The title compound was prepared as a white crystalline solid following the general procedure described in EXAMPLE 5; mp 176°–177° C. (from ether/hexane); $^1$H NMR (360 MHz, $d_6$-DMSO) δ12.82 (bs, 1H, NH), 7.88 (d, J=8.1 Hz, 1H, indazole), 7.48 (d, J=8.1 Hz, 1H, indazole), 7.33 (t, J=8.1 Hz, 1H, indazole), 7.09 (t, J=8.1 Hz, 1H, indazole), 6.98 (d, J=8.6 Hz, 2H, Ph), 6.80 (d, J=8.6 Hz, 2H, Ph), 3.88 (s, 2H, Ar—$CH_2$N), 3.04 (m, 4H, piperazine), 2.50 (m, 4H, piperazine), 2.18 (s, 3H, Me); MS (CI+) m/e 307 (M+H$^+$); Anal. calcd for $C_{19}N_{22}N_4$: C, 74.48; H, 7.24; N, 18.29. Found: C, 74.30; H, 7.27; N, 18.27.

Example 9

3-[4-(2-Pyrimidyl)piperazin-1-ylmethyl]-1H-indazole

The title compound was prepared as a white crystalline solid following the general procedure described in EXAMPLE 5; mp 129°–130° C. (from ether/hexane); $^1$H NMR (360 MHz, $d_6$-DMSO) δ12.82 (bs, 1H, NH), 8.33 (d, J=4.6 Hz, 2H, pyrimidine), 7.89 (d, J=8.0 Hz, 1H, indazole), 7.48 (d, J=8.0 Hz, 1H, indazole), 7.33 (t, J=8.0 Hz, 1H, indazole), 7.10 (t, J=8.0 Hz, 1H, indazole), 6.59 (t, J=4.6 Hz, 1H, pyrimidine), 3.87 (s, 2H, Ar—$CH_2$N), 3.71 (m, 4H, piperazine), 2.49 (m, 4H, piperazine); MS (CI+) m/e 295 (M+H$^+$); Anal. calcd for $C_{16}H_{18}N_6$: C, 65.29; H, 6.16; N, 28.55. Found: C, 65.22; H, 6.15; N, 28.40.

Example 10

3-[4-Piperonylpiperazin-1-ylmethyl]-1H-indazole

The title compound was prepared as a white crystalline solid following the general procedure described in EXAMPLE 5; mp 175°–176° C. (from $CH_2Cl_2$/hexane); $^1$H NMR (360 MHz, $d_6$-DMSO) δ12.77 (bs, 1H, NH), 7.83 (d, J=8.1 Hz, 1H, indazole), 7.46 (d, J=8.1 Hz, 1H, indazole), 7.31 (t, J=8.1 Hz, 1H, indazole), 7.07 (t, J=8.1 Hz, 1H, indazole), 6.81 (s, 1H, piperonyl), 6.81 (d, J=8.0 Hz, 1H, piperonyl), 6.70 (d, J=8.0 Hz, 1H, piperonyl), 5.97 (s, 2H, O—$CH_2$—O), 3.81 (s, 2H, indazole-$CH_2$N), 3.34 (s, 2H, Ph—$CH_2$N), 2.42 (bs, 4H, piperazine), 2.34 (bs, 4H, piperazine); MS (CI+) m/e 351 (M+H$^+$); Anal. calcd for $C_{20}H_{22}N_4O_2 \cdot \frac{1}{4} H_2O$: C, 67.68; H, 6.39; N, 15.78. Found: C, 67.98; H, 6.25; N, 15.85.

Example 11

3-[4-(3-Trifluoromethylphenyl)piperazin-1-ylmethyl]-1H-indazole

The title compound was prepared as a white crystalline solid following the general procedure described in EXAMPLE 5; mp 78°–80° C. (from ether/hexane); $^1$H NMR (360 MHz, $d_6$-DMSO) δ12.84 (bs, 1H, NH), 7.89 (d, J=8.1 Hz, 1H, indazole), 7.49 (d, J=8.1 Hz, 1H, indazole), 7.39 (t, J=8.1 Hz, 1H, Ph), 7.33 (t, J=8.1 Hz, 1H, indazole), 7.19 (d, J=8.1 Hz, 1 H, Ph), 7.13 (s, 1H, Ph), 7.09 (t, J=8.1 Hz, 1H, indazole), 7.04 (d, J=8.1 Hz, 1H, Ph), 3.90 (s, 2H, Ar—$CH_2$N), 3.21 (m, 4H, piperazine), 2.59 (m, 4H, piperazine); MS (CI+) m/e 361 M+H$^+$); Anal. calcd for $C_{19}H_{19}N_4F_3 \cdot \frac{1}{4} H_2O$: C, 62.54; H, 5.39; N, 15.35. Found: C, 62.70; H, 5.32; N, 15.39.

Example 12

3-[4-(2-Pyridyl)piperazin-1-ylmethyl]-1H-indazole

The title compound was prepared as a white crystalline solid following the general procedure described in EXAMPLE 5; mp 148°–150° C. (from $CH_2Cl_2$/hexane); $^1$H NMR (360 MHz, $d_6$-DMSO) δ12.83 (bs, 1H, NH), 8.08 (m, 1H, pyridyl), 7.89 (d, J=8.1 Hz, 1H, indazole), 7.50 (m, 1H, pyridyl), 7.48 (d, J=8.1 Hz, 1H, indazole), 7.33 (t, J=8.1 Hz, 1H, indazole), 7.09 (t, J=8.1 Hz, 1H, indazole), 6.78 (d, J=8.6 Hz, 1H, pyridyl), 6.6.1 (m, 1H, pyridyl), 3.88 (s, 2H, Ar—$CH_2$N), 3.46 (m, 4H, piperazine), 2.52 (m, 4H, piperazine); MS (CI+) m/e 294 M+H$^+$); Anal. calcd for $C_{17}H_{19}N_5 \cdot \frac{1}{4} H_2O$: C, 68.55; H, 6.60; N, 23.51. Found: C, 68.29; H, 6.36; N, 23.19.

Example 13

3-[4-(4-Methoxyphenyl)piperazin-1-ylmethyl]-1H-indazole

The title compound was prepared as a white crystalline solid following the general procedure described in EXAMPLE 5; mp 167°–168° C. (from EtOAc); $^1$H NMR (360 MHz, $d_6$-DMSO) δ12.82 (bs, 1H, NH), 7.87 (d, J=8.1 Hz, 1H, indazole), 7.48 (d, J=8.1 Hz, 1H, indazole), 7.33 (t, J=8.1 Hz, 1H, indazole), 7.09 (t, J=8.1 Hz, 1H, indazole), 6.86 (d, J=9.2 Hz, 2H, Ph), 6.79 (d, J=9.2 Hz, 2H, Ph), 3.88 (s, 2H, Ar—CH$_2$N), 3.67 (s, 3H, OMe), 2.99 (m, 4H, piperazine), 2.57 (m, 4H, piperazine); MS (CI+) m/e 323 (M+H$^+$); Anal. calcd for $C_{19}H_{22}N_4O$: C, 70.78; H, 6.88; N, 17.38. Found: C, 70.72; H, 6.93; N, 17.33.

Example 14

3-[4-(4-Acetylphenyl)piperazin-1-ylmethyl]-1H-indazole

The title compound was prepared as a white crystalline solid following the general procedure described in EXAMPLE 5; mp 198°–200° C. (from EtOAc); $^1$H NMR (360 MHz, $d_6$-DMSO) δ12.84 (bs, 1H, NH), 7.88 (d, J=8.1 Hz, 1H, indazole), 7.68 (d, J=9.7 Hz, 2H, Ph), 7.49 (d, J=8.1 Hz, 1H, indazole), 7.33 (t, J=8.1 Hz, 1H, indazole), 7.09 (t, J=8.1 Hz, 1H, indazole), 6.94 (d, J=9.7 Hz, 2H, Ph), 3.89 (s, 2H, Ar—CH$_2$N), 3.33 (m, 4H, piperazine), 2.57 (m, 4H, piperazine), 2.44 (s,3H, Me); MS (CI+) m/e 335 (M+H$^+$); Anal. calcd for $C_{20}H_{22}N_4O$: C, 71.83; H, 6.63; N, 16.75. Found: C, 72.03; H, 6.54; N, 16.71.

Example 15

3-[4-(5-Methylpyridin-2-yl)piperazin-1-ylmethyl]-1H-indazole

The title compound was prepared as a white crystalline solid following the general procedure described in EXAMPLE 5; mp 151°–153° C. (from EtOAc); $^1$H NMR (360 MHz, $d_6$-DMSO) δ12.82 (bs, 1H, NH), 7.92 (s, 1H, pyridine), 7.88 (d, J=8.0 Hz, 1 H, indazole), 7.48 (d, J=8.0 Hz, 1H, indazole), 7.34 (t, J=8.0 Hz, 1H, indazole), 7.33 (m, 1H, pyridine), 7.09 (t, J=8.0 Hz, 1H, indazole), 6.71 (d, J=8.6 Hz, 1H, pyridine), 3.87 (s, 2H, Ar—CH$_2$N), 3.39 (m, 4H, piperazine), 2.51 (m, 4H, piperazine), 2.12 (s, 3H, Me); MS (CI+) m/e 308 (M+H$^+$); Anal. calcd for $C_{18}H_{21}N_5$: C, 70.33; H, 6.87; N, 22.78. Found: C, 70.48; H, 6.91; N, 22.89.

Example 16

3-(4-Benzo[1,3]dioxol-5-ylpiperazin-1-ylmethyl)-1H-indazole

The title compound was prepared as a white crystalline solid following the general procedure described in EXAMPLE 5; mp 149°–150° C. (from EtOAc); $^1$H NMR (360 MHz, $d_6$-DMSO) δ12.79 (bs, 1H, NH), 7.87 (d, J=8.1 Hz, 1H, indazole), 7.48 (d, J=8.1 Hz, 1H, indazole), 7.32 (t, J=8.1 Hz, 1H, indazole), 7.09 (t, J=8.1 Hz, 1H, indazole), 6.72 (d, J=8.4 Hz, 1H, Ph), 6.83 (d, J=2.3 Hz, 1H, Ph), 6.30 (dd, J=8.4, 2.3 Hz, 1H, Ph), 5.88 (s, 2H, O—CH$_2$—O), 3.87 (s, 2H, Ar—CH$_2$N), 2.99 (m, 4H, piperazine), 2.54 (m, 4H, piperazine); MS (CI+) m/e 337 (M+H$^+$); Anal. calcd for $C_{19}H_{20}N_4O_2 \cdot \frac{1}{4} H_2O$: C, 66.94; H, 6.06; N, 16.44. Found: C, 67.21; H, 5.93; N, 16.10.

Example 17

3-[4-(3,5-Bis-trifluoromethylphenyl)piperazin-1-ylmethyl]-1H-indazole

The title compound was prepared as a white crystalline solid following the general procedure described in EXAMPLE 5; mp 155°–156° C. (from EtOAc); $^1$H NMR (360 MHz, $d_6$-DMSO) δ12.85 (bs, 1H, NH), 7.89 (d, J=8.1 Hz, 1H, indazole), 7.49 (d, J=8.1 Hz, 1H, indazole), 7.43 (s, 2H, Ph), 7.33 (t, J=8.1 Hz, 1H, indazole), 7.28 (s, 1H, Ph), 7.09 (t, J=8.1 Hz, 1H, indazole), 3.90 (s, 2H, Ar—CH$_2$N), 3.34 (m, 4H, piperazine), 2.59 (m, 4H, piperazine); MS (CI+) m/e 429 (M+H$^+$); Anal. calcd for $C_{20}H_{18}N_4F_6$: C, 56.08; H, 4.24; N, 13.08. Found: C, 56.45; H, 4.16; N, 12.63.

Example 18

3-[4-(5-Trifluoromethylpyridin-2-yl)piperazin-1-ylmethyl]-1H-indazole dihydrochloride The title compound was prepared as a white crystalline solid following the general procedure described in EXAMPLE 5; mp 150°–152° C. (from EtOAc); $^1$H NMR (360 MHz, $d_6$-DMSO) δ13.55 (bs, 1H, NH), 10.68 (bs, 2H, NH$^+$), 8.47 (s, 1H, pyridine), 8.00 (d, J=8.1 Hz, 1H, indazole), 7.91 (d, J=9.1 Hz, 1H, pyridine), 7.61 (d, J=8.1 Hz, 1H, indazole), 7.44 (t, J=8.1 Hz, 1H, indazole), 7.24 (t, J=8.1 Hz, 1H, indazole), 7.06 (d, J=9.1 Hz, 1H, pyridine), 4.77 (s, 2H, Ar—CH$_2$N), 4.54 (m, 2H, piperazine), 3.66–3.09 (m, 6H, piperazine); MS (CI+) m/e 362 (M+H$^+$); Anal. calcd for $C_{18}H_{18}F_3N_5 \cdot 2HCl \cdot \frac{1}{2} H_2O$: C, 45.53; H, 5.20; N, 14.75. Found: C, 45.65; H, 5.05; N, 14.37.

Example 19

3-[4-(4-Trifluoromethylpyridin-2-yl)piperazin-1-ylmethyl]-1H-indazole

The title compound was prepared as a white crystalline solid following the general procedure described in EXAMPLE 5; mp 99°–100° C. (from EtOAc); $^1$H NMR (360 MHz, $d_6$-DMSO) δ12.81 (bs, 1H, NH), 8.30 (d, J=5.0 Hz, 1H, pyridine), 7.89 (d, J=8.0 Hz, 1H, indazole), 7.48 (d, J=8.1 Hz, 1H, indazole), 7.33 (t, J=8.1 Hz, 1H, indazole), 7.09 (t, J=8.1 Hz, 1H, indazole), 7.04 (s, 1H, pyridine), 6.85 (d, J=5.0 Hz, 1H, pyridine), 3.89 (s, 2H, Ar—CH$_2$N), 3.58 (m, 4H, piperazine), 2.51 (m, 4H, piperazine); MS (CI+) m/e 362 (M+H$^+$); Anal. calcd for $C_{18}H_{18}F_3N_5 \cdot \frac{1}{2} H_2O$: C, 58.37; H, 5.17; N, 18.91. Found: C, 58.47; H, 5.23; N, 18.66.

Example 20

3-[4-(5-Chloropyridin-2-yl)piperazin-1-ylmethyl]-1H-indazole

The title compound was prepared as a white crystalline solid following the general procedure described in EXAMPLE 5; mp 203°–204° C. (from EtOAc); $^1$H NMR (360 MHz, $d_6$-DMSO) δ12.83 (bs, 1H, NH), 8.08 (d, J=2.7 Hz, 1H, pyridine), 7.88 (d, J=8.1 Hz, 1H, indazole), 7.56 (dd, J=9.1, 2.7 Hz, 1H, pyridine), 7.48 (d, J=8.1 Hz, 1H, indazole), 7.33 (t, J=8.1 Hz, 1H, indazole), 7.09 (t, J=8.1 Hz, 1H, indazole), 6.83 (d, J=9.1 Hz, 1H, pyridine), 3.88 (s, 2H, Ar—CH$_2$N), 3.46 (m, 4H, piperazine), 2.51 (m, 4H, piperazine); MS (CI+) m/e 328 (M+H$^+$); Anal. calcd for $C_{17}H_{18}ClN_5$: C, 62.29; H, 5.53; N, 21.36. Found: C, 62.14; H, 5.36; N, 21.34.

Example 21

3-[4-(5-Methoxypyridin-2-yl)piperazin-1-ylmethyl]-1H-indazole

The title compound was prepared as a white crystalline solid following the general procedure described in EXAMPLE 5: mp 132°–134° C. (from EtOAc); mp 132°–134° C. (from EtOAc); $^1$H NMR (360 MHz, d$_6$-DMSO) δ12.82 (bs, 1H, NH), 7.88 (d, J=8.2 Hz, 1H, indazole), 7.86 (d, J=3.0 Hz, 1H, pyridine), 7.48 (d, J=8.2 Hz, 1H, indazole), 7.33 (t, J=8.2 Hz, 1H, indazole), 7.23 (dd, J=9.1, 3.0 Hz, 1H, pyridine), 7.09 (t, J=8.2 Hz, 1H, indazole), 6.77 (d, J=9.1 Hz, 1H, pyridine), 3.87 (s, 2H, Ar—CH$_2$N), 3.71 (s, 3H, OMe), 3.32 (m, 4H, piperazine), 2.53 (m, 4H, piperazine); MS (CI+) m/e 324 (M+H$^+$); Anal. calcd for C$_{18}$H$_{21}$N$_5$O: C, 66.85; H, 6.55; N, 21.66. Found: C, 66.51; H, 6.53; N, 21.33.

Example 22

2-[4-(1H-Indazol-3-ylmethyl)piperazin-1-yl] quinoline

The title compound was prepared as a white crystalline solid following the general procedure described in EXAMPLE 5; mp 187°–188° C. (from EtOAc); $^1$H NMR (360 MHz, d$_6$-DMSO) δ12.83 (bs, 1H, NH), 8.01 (d, J=9.2 Hz, 1H, quinoline), 7.90 (d, J=8.1 Hz, 1H, indazole), 7.67 (d, J=8.1 Hz, 1H, indazole), 7.52 (t, J=8.1 Hz, 1H, indazole), 7.50 (m, 2H, quinoline), 7.33 (t, J=8.1 Hz, 1H, indazole), 7.20 (m, 2H, quinoline), 7.10 (t, J=7.5 Hz, 1H, quinoline), 3.90 (s, 2H, Ar—CH$_2$N), 3.68 (m, 4H, piperazine), 3.57 (m, 4H, piperazine); MS (CI+) m/e 344 (M+H$^+$); Anal. calcd for C$_{21}$H$_{21}$N$_5$: C, 73.44; H, 6.16; N, 20.39. Found: C, 72.99; H, 6.11; N, 20.22.

Example 23

3-[4-(1H-Indazol-3-ylmethyl)piperazin-1-yl] isoquinoline

The title compound was prepared as a bright yellow crystalline solid following the general procedure described in EXAMPLE 5; mp 214°–215° C. (from EtOAc); $^1$H NMR (360 MHz, d$_6$-DMSO) δ12.83 (bs, 1H, NH), 7.90 (d, J=8.1 Hz, 1H, indazole), 7.85 (d, J=8.2 Hz, 1H, isoquinoline), 7.64 (d, J=8.4 Hz, 1H, indazole), 7.52 (t, J=8.1 Hz, 1H, indazole), 7.49 (d, J=8.7 Hz, 1H, isoquinoline), 7.33 (t, J=8.1 Hz, 1H, indazole), 7.28 (t, J=7.3 Hz, 1H, isoquinoline), 7.10 (t, J=7.2 Hz, 1H, isoquinoline), 6.94 (s, 1H, isoquinoline), 3.91 (s, 2H, Ar—CH$_2$N), 3.53 (m, 4H, piperazine), 2.60 (m, 4H, piperazine); MS (CI+) m/e 344 (M+H$^+$); Anal. calcd for C$_{21}$H$_{21}$N$_5$·¼ H$_2$O: C, 72.49; H, 6.23; N, 20.13. Found: C, 72.72; H, 6.06; N, 20.21.

Example 24

6-Fluoro-3-[4-(4-methoxyphenyl)piperazin-1-ylmethyl]-1H-indazole

Step A: 1-(2-Amino-4-fluorophenyl)ethanone

A solution of BCl$_3$ (110 mL of a 1.0M solution in CH$_2$Cl$_2$, 110 mmol) was cooled to 0° C. and treated with a solution of 3-fluoroaniline (10 mL, 104 mmol) in 1,1,2,2-tetrachloroethane (200 mL). The resulting solution was stirred 15 min and treated with MeCN (16.3 mL, 330 mmol) and AlCl$_3$ (14.7 g, 110 mmol) and heated at 120° C. for 16 h with distillative removal of CH$_2$Cl$_2$. The mixture was cooled to 0° C. and quenched with 2M aqueous HCl (250 mL). The mixture was heated at 80° C. for 1 h to hydrolyse the imine, and extracted with CH$_2$Cl$_2$ (5×100 mL). The combined organic extracts were dried (MgSO$_4$), concentrated and purified by flash chromatography (10% EtOAc in hexane) to give the title compound (9.618 g, 60%) as a low melting pale yellow crystalline solid; $^1$H NMR (360 MHz, d$_6$-DMSO) δ7.81 (dd, J=8.9, 6.7 Hz, 1H, Ph), 7.43 (bs, 2H, NH$_2$), 6.49 (dd, J=12.0, 2.6 Hz, 1H, Ph), 6.35 (dt, J=8.9, 0.7 Hz, 1H, Ph), 2.48 (s, 3H, Me).

Step B: 6-Fluoro-3-methyl-1H-indazole 1-(2-Amino-4-fluorophenyl)ethanone (9.618 g, 62.9 mmol) was treated with concentrated hydrochloric acid (16 mL) and water (16 mL), and the resulting white suspension was cooled to –10° C. and treated with a solution of sodium nitrite (4.338 g, 62.9 mmol) in 10 mL H$_2$O, maintaining the temperature below 0° C. The resulting solution was filtered directly into a rapidly stirred solution of SnCl$_2$·2H$_2$O (34 g in 200 mL H$_2$O) and the resulting mixture was stirred for 1 h at 20° C., basified (32 g NaOH in 200 mL H$_2$O) and extracted with EtOAc. The combined organic extracts were dried (MgSO$_4$), concentrated and the residue purified by flash chromatography (25% EtOAc in hexane) to give the title compound (3.10 g, 33%) as a white solid; mp 116°–117° C. (from hexane); $^1$H NMR (360 MHz, CDCl$_3$) δ12.89 (bs, 1H, NH), 7.62 (dd, J=8.8, 5.1 Hz, 1H, indazole), 7.09 (dd, J=9.1, 2.0 Hz, 1H, indazole), 6.93 (dt, J=9.1, 2.0 Hz, 1H, indazole), 2.60 (s, 3H, Me); MS (CI+) m/e 151 (M+H$^+$); Anal. calcd for C$_8$H$_7$FN$_2$: C, 63.99; H, 4.70; N, 18.66. Found: C, 63.94; H, 4.72; N, 19.10.

Step C: 1-Acetyl-6-fluoro-3-methyl-1H-indazole

6-Fluoro-3-methyl-1H-indazole (2.79 g, 18.6 mmol) in CH$_2$Cl$_2$ (50 mL) was treated with acetic anhydride (2.8 g, 30 mmol), Hünig's base (5.2 mL, 30 mmol) and DMAP (0.2 g, 1.7 mmol). The mixture was stirred 1 h at 20° C., poured into water (100 mL) and extracted with CH$_2$Cl$_2$ (2×100 mL). The extracts were dried (Na$_2$SO$_4$), concentrated and the residue recrystallised from hexane to give the title compound (3.41 g, 96%) as a white crystalline solid; mp 89°–91° C. (from hexane); $^1$H NMR (360 MHz, CDCl$_3$) δ8.05 (dd, J=9.4, 2.2 Hz, 1H, indazole), 7.51 (dd, J=8.7, 5.1 Hz, 1H, indazole), 7.03 (dt, J=8.8, 2.2 Hz, 1H, indazole), 2.67 (s, 3H, Me), 2.49 (s, 3H, Ac); MS (CI+) m/e 193 (M+H$^+$); Anal. calcd for C$_{10}$H$_9$FN$_2$O: C, 62.49; H, 4.72; N, 14.58. Found: C, 62.50; H, 4.79; N, 14.63.

Step D: 1-Acetyl-3-bromomethyl-6-fluoro-1H-indazole

1-Acetyl-6-fluoro-3-methyl-1H-indazole (5.77 g, 33.1 mmol) in CCl$_4$ (100 mL) was treated with NBS (3.64 g, 20 mmol) and benzoyl peroxide (0.388 g, 1.6 mmol) and the mixture was heated at 70° C. for 6 h. The mixture was concentrated and the residue quickly filtered through a plug of flash silica eluting with 2%→7% EtOAc in hexane to give the crude title compound (2.97 g, 65%) contaminated with traces of dibromide and starting material. This was conveniently used directly in subsequent reactions without further purification.

1-Acetyl-3-bromomethyl-6-chloro-1H-indazole, 1-acetyl-3-bromomethyl-7-iodo-1H-indazole, 1-acetyl-3-bromomethyl-7-fluoro-1H-indazole, 1-acetyl-3-bromomethyl-6,7-difluoro-1H-indazole, and 1-acetyl-3-bromomethyl-7-chloro-1H-indazole were similarly prepared from 3-chloroaniline, 2-iodoaniline, 2-fluoroaniline, 2,3-difluoroaniline and 2-chloroaniline, respectively.

Step E: 1-Acetyl-6-fluoro-3-[4-(4-methoxyphenyl) piperazin-1-ylmethyl]-1H-indazole 1-Acetyl-3-bromomethyl-6-fluoro-1-H-indazole (0.63 g, 2.33 mmol) in CH$_2$Cl$_2$ (10 mL) was treated with 4-methoxyphenylpiperazine dihydrochloride (0.593 g, 2.33 mmol) and Hünig's base (1.32 mL, 7.5 mmol) and the mixture stirred at 20° C. for 16 h. The mixture was poured into saturated aqueous sodium bicarbonate solution (25 mL) and extracted with CH$_2$Cl$_2$ (3×25 mL). The combined organic extracts were dried (MgSO$_4$), concentrated and the residue purified by flash chromatography (25% EtOAc in hexane) to give the title compound as a white solid (475 mg, 53%); mp 94°–95° C. (from Et$_2$O/hexane); $^1$H NMR (360 MHz, d$_6$-DMSO) δ8.12 (dd, J=8.4, 2.9 Hz, 1H, indazole), 8.00 (d, J=9.8 Hz, 1H, indazole), 7.34 (t, J=9.8 Hz, 1H, indazole), 6.87 (d, J=9.2 Hz, 2H, Ph), 6.80 (d, J=9.2 Hz, 2H, Ph), 3.93 (s, 2H, Ar—CH$_2$N), 3.67 (s, 3H, OMe), 3.02 (m, 4H, piperazine), 2.70 (s, 3H, Ac), 2.63 (m, 4H, piperazine); MS (CI+) m/e 383 (M+H$^+$); Anal. calcd for C$_{21}$H$_{23}$FN$_4$O$_2$: C, 65.95; H, 6.06; N, 14.65. Found: C, 66.38; H, 5.79; N, 14.59.

Step F: 6-Fluoro-3-|4-(4-methoxyphenyl)piperazin-1-ylmethyl|-1-1H-indazole

1-Acetyl-6-fluoro-3-|4-(4-methoxyphenyl)piperazin-1-ylmethyl|-1H-indazole (445 mg, 1.16 mmol) in CH$_2$Cl$_2$/MeOH (1:1, 25 mL) was treated with sodium methoxide (2 mg) and stirred for 15 min at 20° C. The mixture was poured into saturated aqueous sodium bicarbonate solution (25 mL) and extracted with CH$_2$Cl$_2$ (3×50 mL). The combined organic extracts were dried (MgSO$_4$), concentrated and the residue recrystallised from EtOAc/hexane to give the title compound as colourless crystals (290 mg, 73%); mp 155°–156° C. (from EtOAc/hexane); $^1$H NMR (360 MHz, d$_6$-DMSO) δ12.89 (bs, 1H, NH), 7.90 (dd,J=8.9, 5.5 Hz, 1H, indazole), 7.25 (dd, J=9.7, 2.1 Hz, 1H, indazole), 6.97 (dt, J=9.3, 2.2 Hz, 1H, indazole), 6.86 (d, J=9.2 Hz, 2H, Ph), 6.79 (d, J=9.2 Hz, 2H, Ph), 3.86 (s, 2H, Ar—CH$_2$N), 3.67 (s, 3H, OMe), 2.99 (m, 4H, piperazine), 2.56 (m, 4H, piperazine); MS (CI+) m/e 341 (M+H$^+$); Anal. calcd for C$_{19}$H$_{21}$FN$_4$O: C, 67.04; H, 6.22; N, 16.46. Found: C, 67.01; H, 5.99; N, 16.36.

Example 25

3-|4-(4-Chlorophenyl)piperazin-1-ylmethyl|-6-fluoro-1H-indazole

The title compound was prepared as a white crystalline solid following the general procedure described in EXAMPLE 24; mp 217°–219° C. (from EtOAc/hexane); $^1$H NMR (360 MHz, d$_6$-DMSO) δ12.90 (bs, 1H, NH), 7.90 (dd, J=8.9, 5.5 Hz, 1H, indazole), 7.25 (dd, J=9.7, 2.1 Hz, 1H, indazole), 7.20 (d, J=9.1 Hz, 2H, Ph), 6.97 (dt, J=9.3, 2.2 Hz, 1H, indazole), 6.91 (d, J=9.1 Hz, 2H, Ph), 3.86 (s, 2H, Ar—CH$_2$N), 3.11 (m, 4H, piperazine), 2.56 (m, 4H, piperazine); MS (CI+) m/e 345 (M+H$^+$); Anal. calcd for C$_{18}$H$_{18}$N$_4$ClF: C, 62.7; H, 5.26; N, 16.26. Found: C, 62.85; H, 5.17; N, 16.11.

Example 26

6-Fluoro-3-|4-(2-phenylacetyl)piperazin-1-ylmethyl|-1H-indazole

The title compound was prepared as a white crystalline solid following the general procedure described in EXAMPLE 24; mp 173°–174° C. (from EtOAc); $^1$H NMR (360 MHz, d$_6$-DMSO) δ12.89 (bs, 1H, NH), 7.87 (dd, J=8.8, 5.4 Hz, 1H, indazole), 7.30–7.18 (m, 6H, aromatic), 6.96 (dt, J=9.3, 2.2 Hz, 1H, indazole), 3.80 (s, 2H, Ar—CH$_2$N), 3.68 (s, 2H, CH2-Ph), 3.45 (bs, 4H, piperazine), 2.33 (m, 4H, piperazine); MS (CI+) m/e 353 (M+H$^+$); Anal. calcd for C$_{20}$H$_{21}$FN$_4$O: C, 68.16; H, 6.01; N, 15.90. Found: C, 68.17; H, 6.12; N, 15.64.

Example 27

6-Fluoro-3-|4-(2-phenylethyl)piperazin-1-ylmethyl|-1H-indazole

A solution of 6-fluoro-3-|4-(2-phenylacetyl)piperazin-1-ylmethyl|-1H-indazole (156 mg, 0.44 mmol) in THF (5 mL) was treated with LiAlH$_4$ (0.44 mL of a 1.0M solution in THF, 0.44 mmol) and heated at 40° C. for 16 h. The solution was cooled, diluted with EtOAc (50 mL), 2M aqueous NaOH was added (200 mL) and the resulting suspension was stirred for 1 h at 20° C., filtered, concentrated and the residue purified by flash chromatography (EtOAc→10% MeOH in EtOAc) to give the title compound (130 mg, 87%) as a white solid; mp 148°–149° C. (from Et$_2$O/hexane); $^1$H NMR (360 MHz, d$_6$-DMSO) δ12.85 (bs, 1H, NH), 7.89 (dd, J=8.9, 5.5 Hz, 1H, indazole), 7.28–7.14 (m, 6H, aromatic), 6.96 (dt, J=9.3, 2.2 Hz, 1H, indazole), 3.79 (s, 2H, Ar—CH$_2$N), 2.70 (t, J=7.2 Hz, 2H, CH$_2$—Ph), 2.51–2.40 (m, 10H, piperazine, CH$_2$); MS (CI+) m/e 339 (M+H$^+$); Anal. calcd for C$_{20}$H$_{23}$FN$_4$: C, 70.98; H, 6.85, N, 16.56. Found: C, 71.35; H, 6.88; N, 16.56.

Example 28

6-Chloro-3-|4-(4-methoxyphenyl)piperazin-1-ylmethyl|-1H-indazole

The title compound was prepared as a white crystalline solid following the general procedure described in EXAMPLE 24; mp 182°–184° C. (from EtOAc); $^1$H NMR (360 MHz, d$_6$-DMSO) δ12.96 (bs, 1H, NH), 7.90 (d, J=8.7 Hz, 1H, indazole), 7.56 (d, J=1.5 Hz, 1H, indazole), 7.11 (dd, J=8.7, 1.5 Hz, 1H, indazole), 6.85 (d, J=9.2 Hz, 2H, Ph), 6.79 (d, J=9.2 Hz, 2H, Ph), 3.87 (s, 2H, Ar—CH$_2$N), 3.67 (s, 3H, OMe), 2.99 (m, 4H, piperazine), 2.56 (m, 4H, piperazine); MS (CI+) m/e 357 (M+H$^+$); Anal. calcd for C$_{19}$H$_{21}$N$_4$OCl: C, 63.95; H, 5.93; N, 15.70. Found: C, 64.24; H, 5.86; N, 15.54.

Example 29

7-Iodo-3-|4-(4-methoxyphenyl)piperazin-1-ylmethyl|-1H-indazole

The title compound was prepared as a white crystalline solid following the general procedure described in EXAMPLE 24: dihydrogen oxalate salt: mp 185°–186° C. (from EtOAc); $^1$H NMR (360 MHz, d$_6$-DMSO) δ13.01 (bs, 1H, NH), 7.98 (d, J=7.9 Hz, 1H, indazole), 7.81 (d, J=7.2 Hz, 1H, indazole), 6.98 (t, J=7.2 Hz, 1H, indazole), 6.89 (d, J=9.2 Hz, 2H, Ph), 6.82 (d, J=9.2 Hz, 2H, Ph), 4.33 (s, 2H, Ar—CH$_2$N), 3.68 (s, 3H, OMe), 3.13 (bs, 4H, piperazine), 3.00 (bs, 4H, piperazine); MS (CI+) m/e 449 (M+H$^+$); Anal. calcd for C$_{19}$H$_{21}$N$_4$O.2C$_2$H$_2$O$_4$: C, 43.96; H, 4.01; N, 8.92. Found: C, 43.76; H, 3.86; N, 8.60.

Example 30

7-Fluoro-3-|4-(4-methoxyphenyl)piperazin-1-ylmethyl|-1H-indazole

The title compound was prepared as a white crystalline solid following the general procedure described in EXAMPLE 24; mp 178°–179° C. (from EtOAc); $^1$H NMR (360 MHz, d$_6$-DMSO) δ13.40 (bs, 1H, NH), 7.71 (d, J=8.0 Hz, 1H, indazole), 7.17 (dd, J=11.4, 7.6 Hz, 1H, indazole), 7.07 (dt, J=7.8, 4.5 Hz, 1H, indazole), 6.86 (d, J=9.2 Hz, 2H, Ph), 6.79 (d, J=9.2 Hz, 2H, Ph), 3.90 (s, 2H, Ar—CH$_2$N), 3.67 (s, 3H, OMe), 2.99 (m, 4H, piperazine), 2.57 (m, 4H, piperazine); MS (CI+) m/e 341 (M+H$^+$); Anal. calcd for C$_{19}$H$_{21}$FN$_4$O: C, 67.04; H, 6.22; N, 16.46. Found: C, 67.07; H, 6.17; N, 16.14.

Example 31

7-Fluoro-3-|4-(4-methylphenyl)piperazin-1-ylmethyl|-1H-indazole

The title compound was prepared as a white crystalline solid following the general procedure described in EXAMPLE 24; mp 176°–177° C. (from EtOAc); $^1$H NMR (360 MHz, d$_6$-DMSO) δ13.38 (bs, 1H, NH), 7.72 (d, J=8.0 Hz, 1H, indazole), 7.16 (m, 1H, indazole), 7.06 (m, 1H, indazole), 6.99 (d, J=8.6 Hz, 2H, Ph), 6.80 (d, J=8.6 Hz, 2H, Ph), 3.90 (s, 2 H, Ar—CH$_2$N), 3.05 (m, 4H, piperazine), 2.57 (m, 4H, piperazine), 2.18 (s, 3H, Me); MS (CI+) m/e 325 (M+H$^+$); Anal. calcd for C$_{19}$H$_{21}$N$_4$F: C, 70.35; H, 6.53; N, 17.27. Found: C, 70.19; H, 6.59; N, 16.87.

Example 32

6,7-Difluoro-3-|4-(4-methoxyphenyl)piperazin-1-ylmethyl|-1H-indazole

The title compound was prepared as a white crystalline solid following the general procedure described in EXAMPLE 24; mp 195°–197° C. (from EtOAc); $^1$H NMR (360 MHz, d$_6$-DMSO) δ13.55 (bs, 1H, NH), 7.72 (dd, J=8.9, 4.4 Hz, 1H, indazole), 7.15 (m, 1H, indazole), 6.86 (d, J=6.7 Hz, 2H, Ph), 6.79 (d, J=6.7 Hz, 2H, Ph), 3.89 (s, 2H, Ar—CH$_2$N), 3.67 (s, 3 H, OMe), 2.99 (m, 4H, piperazine), 2.57 (m, 4H, piperazine); MS (CI+) m/e 359 (M+H$^+$); Anal. calcd for C$_{19}$H$_{20}$F$_2$N$_4$O: C, 63.68; H, 5.63; N, 15.63. Found: C, 63.52; H, 5.50; N, 15.44.

Example 33

6,7-Difluoro-3-|4-(4-chlorophenyl)piperazin-1-ylmethyl|-1H-indazole

The title compound was prepared as a white crystalline solid following the general procedure described in EXAMPLE 24; mp 167°–168° C. (from EtOAc); $^1$H NMR (360 MHz, d$_6$-DMSO) δ13.55 (bs, 1H, NH), 7.72 (dd, J=8.9, 4.4 Hz, 1H, indazole), 7.20 (d, J=9.0 Hz, 2H, Ph), 7.15 (m, 1H, indazole), 6.91 (d, J=9.0 Hz, 2H, Ph), 3.89 (s, 2H, Ar—CH$_2$N), 3.11 (m, 4 H, piperazine), 2.56 (m, 4H, piperazine); MS (CI+) m/e 363 (M+H$^+$); Anal. calcd for C$_{18}$H$_{17}$N$_4$F$_2$Cl: C, 59.59; H, 4.72; N, 15.44. Found: C, 59.54; H, 4.77; N, 15.15.

Example 34

7-Chloro-3-|4-(4-methoxyphenyl)piperazin-1-ylmethyl|-1H-indazole

The title compound was prepared as a white crystalline solid following the general procedure described in EXAMPLE 24; mp 190°–191° C. (from EtOAc/MeOH); $^1$H NMR (360 MHz, d$_6$-DMSO) δ13.36 (bs, 1H, NH), 7.87 (d, J=7.8 Hz, 1H, indazole), 7.43 (d, J=6.8 Hz, 1H, indazole), 7.11 (t, J=7.8 Hz, 1H, indazole), 6.86 (d, J=6.7 Hz, 2H, Ph), 6.79 (d, J=6.7 Hz, 2H, Ph), 3.90 (s, 2H, Ar—CH$_2$N), 3.67 (s, 3H, OMe), 2.99 (m, 4 H, piperazine), 2.57 (m, 4H, piperazine); MS (CI+) m/e 357 (M+H$^+$); Anal. calcd for C$_{19}$H$_{21}$N$_4$ClO: C, 63.95; H, 5.93; N, 15.70. Found: C, 63.89; H, 5.88; N, 15.34.

Example 35

7-Chloro-3-|4-(4-chlorophenyl)piperazin-1-ylmethyl|-1H-indazole

The title compound was prepared as a white crystalline solid following the general procedure described in EXAMPLE 24; mp 152°–154° C. (from EtOAc); $^1$H NMR (360 MHz, d$_6$-DMSO) δ13.36 (bs, 1H, NH), 7.87 (d, J=8.0 Hz, 1H, indazole), 7.43 (d, J=7.4 Hz, 1H, indazole), 7.20 (d, J=9.0 Hz, 2H, Ph), 7.11 (t, J=8.0 Hz, 1H, indazole), 6.91 (d, J=9.0 Hz, 2 H, Ph), 3.90 (s, 2H, Ar—CH$_2$N), 3.11 (m, 4H, piperazine), 2.57 (m, 4H, piperazine); MS (CI+) m/e 361 (M+H$^+$); Anal. calcd for C$_{18}$H$_{18}$N$_4$Cl$_2$: C, 59.84; H, 5.02; N, 15.51. Found: C, 59.77; H, 4.76; N, 15.33.

Example 36

3-|4-Benzo|1,3|dioxol-5-ylpiperazin-1-ylmethyl|-7-chloro-1H-indazole

The title compound was prepared as a white crystalline solid following the general procedure described in EXAMPLE 24; mp 173°–174° C. (from EtOAc); $^1$H NMR (360 MHz, d$_6$-DMSO) δ13.33 (bs, 1H, NH), 7.86 (d, J=8.0 Hz, 1H, indazole), 7.42 (d, J=7.4 Hz, 1H, indazole), 7.10 (t, J=8.0 Hz, 1H, indazole), 6.72 (d, J=8.4 Hz, 1H, Ph), 6.63 (s, 1H, Ph), 6.30 (d, J=8.4 Hz, 1H, Ph), 5.89 (s, 2H, O—CH$_2$—O), 3.89 (s, 2 H, Ar—CH$_2$N), 2.98 (m, 4H, piperazine), 2.55 (m, 4H, piperazine); MS (CI+) m/e 371 (M+H$^+$); Anal. calcd for C$_{19}$H$_{19}$N$_4$ClO$_2$·¼ H$_2$O: C, 60.80; H, 5.24; N, 14.93. Found: C, 60.89; H, 5.08; N, 14.68.

Example 37

7-Chloro-3-|4-(3-trifluoromethylphenyl)piperazin-1-ylmethyl|-1H-indazole

The title compound was prepared as a white crystalline solid following the general procedure described in EXAMPLE 24. Hydrogen oxalate salt: mp 133°–134° C. (from EtOAc); $^1$H NMR (360 MHz, d$_6$-DMSO) δ7.91 (d, J=8.2 Hz, 1H, indazole), 7.47 (d, J=7.4 Hz, 1H, indazole), 7.42 (t, J=8.0 Hz, 1H, indazole), 7.22–7.14 (m, 3H, aromatic), 7.08 (d, J=7.6 Hz, 1 H, Ph), 4.19, Ar—CH$_2$N), 3.31 (bs, 4H, piperazine), 2.85 (bs, 4H, piperazine); MS (CI+) m/e 395 (M+H$^+$); Anal. calcd for C$_{19}$H$_{18}$N$_4$ClF$_3$·C$_2$O$_4$H$_2$·¼ H$_2$O: C, 51.54; H, 4.22; N, 11.45. Found: C, 51.75; H, 4.05; N, 11.15.

Example 38

7-Chloro-3-|4-(4-methylphenyl)piperazin-1-ylmethyl|-1H-indazole

The title compound was prepared as a white crystalline solid following the general procedure described in EXAMPLE 24: mp 187°–188° C. (from EtOAc); $^1$H NMR (360 MHz, d$_6$-DMSO) δ13.35 (bs, 1H, NH), 7.87 (d, J=8.2 Hz, 1H, indazole), 7.42 (d, J=8.0 Hz, 1H, indazole), 7.11 (t, J=8.2 Hz, 1H, indazole), 6.99 (d, J=8.3 Hz, 2H, Ph), 6.80 (d, J=8.3 Hz, 2H, Ph), 3.90 (s, 2H, Ar—CH$_2$N), 3.05 (m, 4H, piperazine), 2.57 (m, 4H, piperazine), 2.18 (s, 3H, Me); MS (CI+) m/e 341 (M+H$^+$); Anal. calcd for C$_{19}$H$_{21}$N$_4$Cl: C, 66.95; H, 6.21; N, 16.44. Found: C, 67.11; H, 6.21; N, 16.34.

Example 39

7-Chloro-3-|4-(5-chloropyridin-2-yl)piperazin-1-ylmethyl|-1H-indazole

The title compound was prepared as a white crystalline solid following the general procedure described in EXAMPLE 24; ;mp 150°–152° C. (from EtOAc); $^1$H NMR (360 MHz, d$_6$-DMSO) δ13.37 (bs, 1H, NH), 8.09 (d, J=2.6 Hz, 1H, pyridine), 7.88 (d, J=8.0 Hz, 1H, indazole), 7.57 (dd, J=9.2, 2.6 Hz, 1H, pyridine), 7.44 (d, J=7.4 Hz, 1H, indazole), 7.11 (t, J=7.8 Hz, 1H, indazole), 6.83 (d, J=9.2 Hz, 1H, pyridine), 3.90 (s, 2H, Ar—CH$_2$N), 3.46 (m, 4H, piperazine), 2.51 (m, 4H, piperazine); MS (CI+) m/e 362 (M+H$^+$); Anal. calcd for C$_{17}$H$_{17}$N$_5$Cl$_2$: C, 56.36; H, 4.73; N, 19.33. Found: C, 56.70; H, 4.67; N, 19.07.

Example 40

3-[4-(7-Chloro-1H-Indazol-3-ylmethyl)piperazin-1-yl]isoquinoline

The title compound was prepared as a bright yellow crystalline solid following the general procedure described in EXAMPLE 24; mp 208°–209° C. (from EtOAc); $^1$H NMR (360 MHz, $d_6$-DMSO) δ13.37 (bs, 1H, NH), 7.91 (d, J=8.1 Hz, 1H, indazole), 7.86 (d, J=8.2 Hz, 1H, isoquinoline), 7.65 (d, J=8.3 Hz, 1H, isoquinoline), 7.53 (dt, J=6.7, 0.9 Hz, 1H, isoquinoline), 7.44 (d, J=7.3 Hz, 1H, indazole), 7.27 (t, J=7.9 Hz, 1H, isoquinoline), 7.12 (t, J=7.7 Hz, 1H, indazole), 6.94 (s, 1H, isoquinoline), 3.93 (s, 2H, Ar—CH$_2$N), 3.53 (m, 4H, piperazine), 2.60 (m, 4H, piperazine); MS (CI+) m/e 378 (M+H$^+$); Anal. calcd for $C_{21}H_{20}N_5Cl$: C, 66.75; H, 5.34; N, 18.53. Found: C, 66.71; H, 5.01; N, 18.40.

We claim:

1. A method for the treatment of psychotic disorders which comprises administering to a patient in need thereof an effective amount of a dopamine antagonist compound of formula IIA, and pharmaceutically acceptable salts thereof:

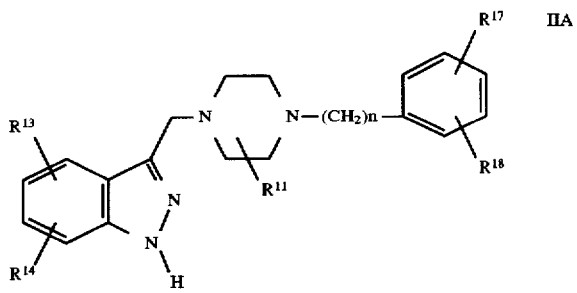

wherein n is zero, 1, 2 or 3;

$R^{11}$ represents hydrogen or $C_{1-6}$ alkyl;

$R^{13}$ and $R^{14}$ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$) alkoxy or $C_{2-6}$ alkylcarbonyl; and $R^{17}$ and $R^{18}$ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$) alkoxy or $C_{2-6}$ alkylcarbonyl, or $R^{17}$ and $R^{18}$, when situated on adjacent carbon atoms, together represent methylenedioxy.

2. The method as claimed in claim 1 wherein the compound of formula IIA, $R^{14}$ and $R^{18}$ both represent hydrogen.

3. A dopamine antagonist compound of formula IIB, or a pharmaceutically acceptable salt thereof:

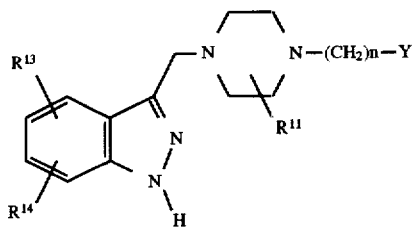

wherein n is zero or 1;

$R^{11}$ represents hydrogen or $C_{1-6}$ alkyl;

$R^{13}$ and $R^{14}$ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$) alkoxy or $C_{2-6}$ alkylcarbonyl; and Y represents a group of formula Ya or Yd:

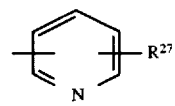

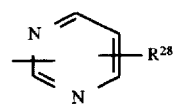

in which $R^{27}$ represents halogen, trifluoromethyl, $C_{1-6}$ alkyl or $C_{1-6}$ alkoxy; and $R^{28}$ represents hydrogen, halogen, trifluoromethyl, $C_{1-6}$ alkyl or $C_{1-6}$ alkoxy.

4. A compound as claimed in claim 3 wherein $R^{14}$ represents hydrogen; Y represents a group of formula Ya; and $R^{27}$ represents halogen, $C_{1-6}$ alkyl or $C_{1-6}$ alkoxy.

5. A pharmaceutical composition comprising a compound as claimed in claim 3 in association with a pharmaceutically acceptable carrier.

6. A Method for the treatment of psychotic disorders which comprises administering to a patient in need thereof an effective amount of a dopamine antagonist compound selected from:

3-[4-(4-chlorophenyl)piperazin-1-ylmethyl]-1H-indazole;
3-(4-phenylpiperazin-1-ylmethyl)-1H-indazole;
3-(4-benzylpiperazin-1-ylmethyl)-1H-indazole;
3-(3-methyl-4-phenylpiperazin-1-ylmethyl)-1H-indazole;
3-[4-(4-fluorophenyl)piperazin-1-ylmethyl]-1H-indazole;
3-[4-(2-methylphenyl)piperazin-1-ylmethyl]-1H-indazole;
3-[4-(3-methylphenyl)piperazin-1-ylmethyl]-1H-indazole;
3-[4-(4-methylphenyl)piperazin-1-ylmethyl]-1H-indazole;
3-[4-(pyrimidin-2-yl)piperazin-1-ylmethyl]-1H-indazole;
3-[4-(3,4-methylenedioxybenzyl)piperazin-1-ylmethyl]-1H-indazole;
3-[4-(3-trifluoromethylphenyl)piperazin-1-ylmethyl]-1H-indazole;
3-[4-(pyrid-2-yl)piperazin-1-ylmethyl]-1H-indazole;
3-[4-(4-methoxyphenyl)piperazin-1-ylmethyl]-1H-indazole;
3-[4-(4-acetylphenyl)piperazin-1-ylmethyl]-1H-indazole;
6-fluoro-3-[4-(4-methoxyphenyl)piperazin-1-ylmethyl]-1H-indazole;
3-[4-(4-chlorophenyl)piperazin-1-ylmethyl]-6-fluoro-1H-indazole;
6-fluoro-3-[4-(2-phenylethyl)piperazin-1-ylmethyl]-1H-indazole;
6-chloro-3-[4-(4-methoxyphenyl)piperazin-1-ylmethyl]-1H-indazole;
7-chloro-3-[4-(4-methoxyphenyl)piperazin-1-ylmethyl]-1H-indazole;
3-[4-(2-phenylethyl)piperazin-1-ylmethyl]-1H-indazole;
3-[4-(5-chloropyrid-2-yl)piperazin-1-ylmethyl]-1H-indazole;
3-[4-(5-methylpyrid-2-yl)piperazin-1-ylmethyl]-1H-indazole;
3-[4-(5-methoxypyrid-2-yl)piperazin-1-ylmethyl]-1H-indazole;
3-[4-(3,4-methylenedioxyphenyl)piperazin-1-ylmethyl]-1H-indazole;
3-[4-(3,5-bis(trifluoromethyl)phenyl)piperazin-1-ylmethyl]-1H-indazole;
3-[4-(5-trifluoromethylpyrid-2-yl)piperazin-1-ylmethyl]-1H-indazole;

3-[4-(4-trifluoromethylpyrid-2-yl)piperazin-1-ylmethyl]-1H-indazole;

7-iodo-3-[4-(4-methoxyphenyl)piperazin-1-ylmethyl]-1H-indazole;

7-fluoro-3-[4-(4-methoxyphenyl)piperazin-1-ylmethyl]-1H-indazole;

7-fluoro-3-[4-(4-methylphenyl)piperazin-1-ylmethyl]-1H-indazole;

6,7-difluoro-3-[4-(4-methoxyphenyl)piperazin-1-ylmethyl]-1H-indazole;

3-[4-(4-chlorophenyl)piperazin-1-ylmethyl]-6,7-difluoro-1H-indazole;

7-chloro-3-[4-(4-chlorophenyl)piperazin-1-ylmethyl]-1H-indazole;

7-chloro-3-[4-(3,4-methylenedioxyphenyl)piperazin-1-ylmethyl]-1H-indazole;

7-chloro-3-[4-(3-trifluoromethylphenyl)piperazin-1-ylmethyl]-1H-indazole;

7-chloro-3-[4-(4-methylphenyl)piperazin-1-ylmethyl]-1H-indazole;

7-chloro-3-[4-(5-chloropyrid-2-yl)piperazin-1-ylmethyl]-1H-indazole;

and pharmaceutically acceptable salts thereof.

7. A pharmaceutical composition comprising a compound as claimed in claim 6 in association with a pharmaceutically acceptable carrier.

* * * * *